(12) United States Patent
Lavedan et al.

(10) Patent No.: US 11,845,990 B2
(45) Date of Patent: *Dec. 19, 2023

(54) PREDICTION OF SLEEP PARAMETER AND RESPONSE TO SLEEP-INDUCING COMPOUND BASED ON PER3 VNTR GENOTYPE

(71) Applicant: Vanda Pharmaceuticals Inc., Washington, DC (US)

(72) Inventors: Christian N. Lavedan, Pinehurst, NC (US); Mihael H. Polymeropoulos, Potomac, MD (US); Gunther P. Birznieks, Chevy Chase, MD (US)

(73) Assignee: Vanda Pharmaceuticals Inc., Washington, DC (US)

( * ) Notice: Subject to any disclaimer, the term of this patent is extended or adjusted under 35 U.S.C. 154(b) by 186 days.

This patent is subject to a terminal disclaimer.

(21) Appl. No.: 17/327,102

(22) Filed: May 21, 2021

(65) Prior Publication Data

US 2021/0277478 A1    Sep. 9, 2021

Related U.S. Application Data

(63) Continuation of application No. 12/675,614, filed as application No. PCT/US2008/076147 on Sep. 12, 2008, now Pat. No. 11,060,144.

(60) Provisional application No. 60/972,196, filed on Sep. 13, 2007.

(51) Int. Cl.
| | |
|---|---|
| *C07H 21/04* | (2006.01) |
| *C12Q 1/68* | (2018.01) |
| *C12Q 1/6883* | (2018.01) |
| *A61K 31/16* | (2006.01) |
| *C07D 307/81* | (2006.01) |

(52) U.S. Cl.
CPC ............ *C12Q 1/6883* (2013.01); *A61K 31/16* (2013.01); *C07D 307/81* (2013.01); *C12Q 2600/106* (2013.01); *C12Q 2600/156* (2013.01); *Y10T 436/143333* (2015.01)

(58) Field of Classification Search
None
See application file for complete search history.

(56) References Cited

U.S. PATENT DOCUMENTS

| | | | | |
|---|---|---|---|---|
| 5,856,529 | A | * | 1/1999 | Catt et al. ..................... 549/469 |
| 2009/0105333 | A1 | * | 4/2009 | Birznieks et al. ............ 514/469 |

FOREIGN PATENT DOCUMENTS

| | | | |
|---|---|---|---|
| WO | 2004038043 A2 | 5/2004 | |
| WO | WO2004038043 | * 5/2004 | ............... C12Q 1/68 |
| WO | 2005063297 A2 | 7/2005 | |
| WO | 2007137244 A1 | 11/2007 | |
| WO | WO2007/137244 | * 11/2007 | ............... C12Q 1/68 |

OTHER PUBLICATIONS

Pereira et al. (Sleep, vol. 28, No. 1, pp. 29-32, 2005).*
Van der Heijden et al. (Biological Rhythm Research, vol. 36, No. 5, pp. 381-388, Dec. 2005).*
Viola et al. (Current Biology, vol. 17, pp. 613-618, EDAT: Mar. 10, 2007).*
Goel et al. (PloS ONE, vol. 4, No. 6, pp. e5874, Jun. 2009).*
Voinescu et al. (Sleep and Biological Rhythms, pp. 1-4, Sep. 6, 2011).*
"VEC-162—New Rozerem—type Sleep Aid provides effective" http://insomnia-relief.com/information/?p=58, Nov. 26, 2006.*
"Data Presented at SLEEP 2007 shows VEC-162 improves sleep onset and maintenance vs. Placebo" Vanda Pharmaceuticals, Inc. Jun. 14, 2007.*
Patent Cooperation Treaty, PCT Notification of Transmittal of The International Search Report and The Written Opinion of the International Searching Authority, or the Declaration, dated Dec. 3, 2008 for Application No. PCT/US2008/076147, filed Sep. 12, 2008, 19 pages.
Archer et al., "A Length Polymorphism in the Circadian Clock Gene Per3 is Linked to Delayed Sleep Phase Syndrome and Extreme Diurnal Preference", Jun. 2003, pp. 413-416, XP008029828, SLEEP, Allen Press, vol. 26, No. 3.
Viola et al., "PER3 Polymorphism Predicts Sleep Structure and Waking Performance", Apr. 2007, pp. 613-618, XP022009295, Current Biology, Current Science, vol. 17, No. 7.
Ebisawa et al., "Association of Structural Polymorphisms in the Human Period3 Gene with Delayed Sleep Phase Syndrome", Jan. 2001, pp. 342-346, XP0001187591, EMBO Reports, vol. 2, No. 41.
Vachharajani et al., "Preclinical Pharmacokinetics and Metobolism of BMS-214778, a Novel Melatonin Receptor Agonist", Apr. 2003, pp. 760-772, XP008074135, Journal of Pharmaceutical Sciences, vol. 92, No. 4.
Rajaratnam et al., "The Melatonin Agonist VEC-162 Immediately Phase-Advances the Human Circadian System", 2006, p. A54, XP008098612, SLEEP, vol. 29, Abstract Supplemental.
Birznieks et al., "Melatonin Agonist VEC-162 Improves Sleep Onset and Maintenance in a Model of Transient Insomnia", 2007, p. A264, XP008098611, SLEEP, vol. 30, Abstract Supplemental.
European Patent Office, Office Action for Application No. 08830209.6 dated Aug. 6, 2010, 10 pages.
Rajaratnam et al. (20th Congress of the European Sleep Research Society, Sep. 2010).
Mitkus et al. (effect of a period 3 (PER3) gene polymorphism on response to Tasimelteon treatment in a phage advance model of transient insomnia, 2009).

(Continued)

*Primary Examiner* — Jeanine A Goldberg
(74) *Attorney, Agent, or Firm* — Hoffman Warnick LLC

(57) ABSTRACT

The invention relates to the prediction of a sleep parameter (e.g., sleep efficiency (SE), latency to persistent sleep (LPS), wake after sleep onset (WASO), total sleep time (TST)) of an individual and the response of such an individual to a sleep inducing compound based on the individual's PER3 variable number tandem repeat (VNTR) genotype.

7 Claims, 5 Drawing Sheets

Specification includes a Sequence Listing.

(56) References Cited

OTHER PUBLICATIONS

Cardinali et al. (UCA, Biblioteca digital de la Universidad Catolica Argentina, "Melatonin and its analogs in insomnia and depression", vol. 52, No. 4, 2012).
FDA information, http://www.accessdata.fda.gov/drugsatfda_docs/label/2014/205677s000lbl.pdf, accessed Mar. 2014.
Rajarantnam et al. (SLEEP, vol. 29, Abstract Supplement, 2006). (Year: 2006).

* cited by examiner

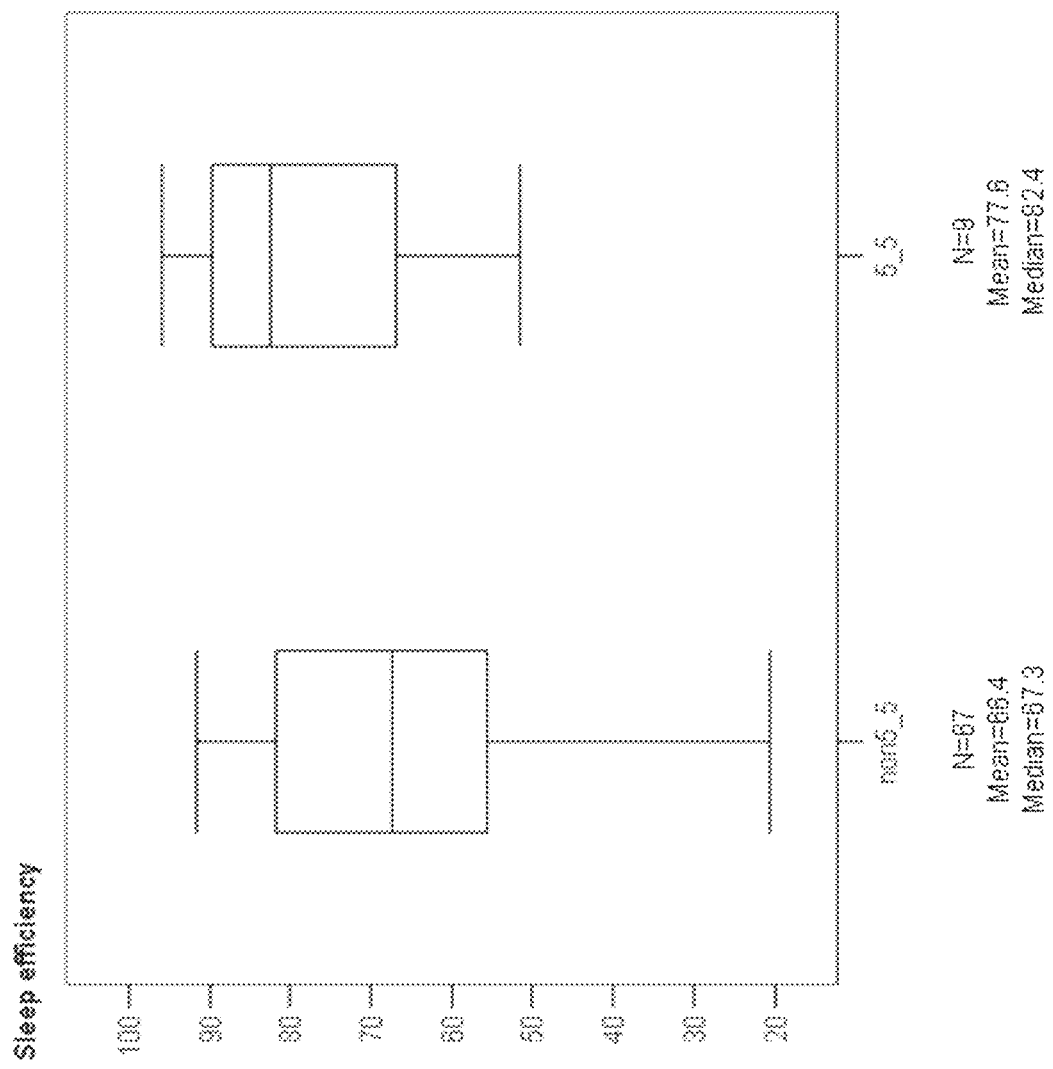

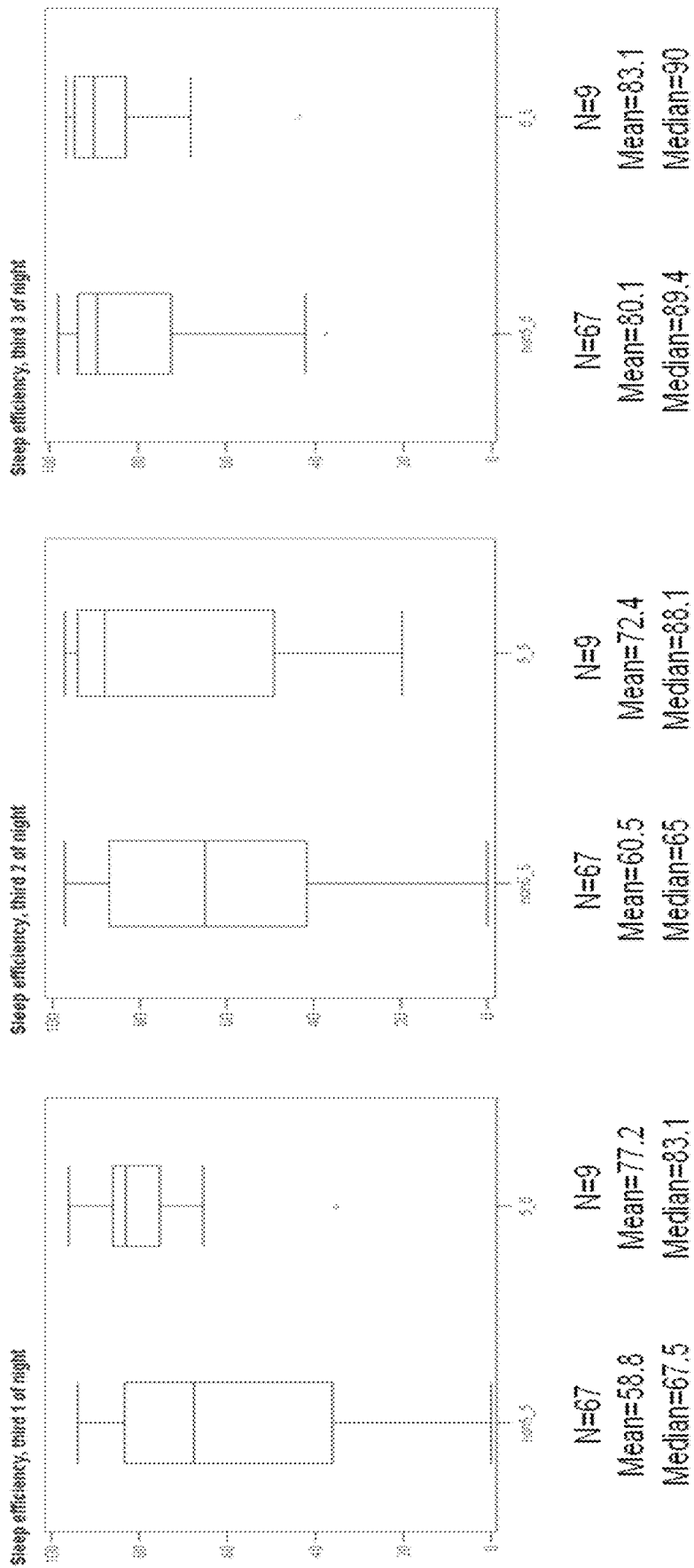

SEQUENCE LISTING

<160> NUMBER OF SEQ ID NOS: 2

<210> SEQ ID NO 1
<211> LENGTH: 32
<212> TYPE: DNA
<213> ORGANISM: Artificial Sequence
<220> FEATURE:
<223> OTHER INFORMATION: primer sequence

<400> SEQUENCE: 1
caaaatttta tgacactacc agaatggctg ac                32

<210> SEQ ID NO 2
<211> LENGTH: 28
<212> TYPE: DNA
<213> ORGANISM: Artificial Sequence
<220> FEATURE:
<223> OTHER INFORMATION: primer sequence

<400> SEQUENCE: 2
aaccttgtac ttccacatca gtgcctgg                28

PREDICTION OF SLEEP PARAMETER AND RESPONSE TO SLEEP-INDUCING COMPOUND BASED ON PER3 VNTR GENOTYPE

CROSS-REFERENCE TO RELATED APPLICATIONS

This application is a continuation application of co-pending U.S. patent application Ser. No. 12/675,614, filed 26 Feb. 2010, which is the US national phase of International Patent Application Serial No. PCT/US2008/076147, filed 12 Sep. 2008, which in turn claims the benefit of U.S. Provisional Patent Application Ser. No. 60/972,196, filed 13 Sep. 2007, each of which is hereby incorporated herein.

SEQUENCE LISTING

The sequence listing contained in the electronic file titled "VAND-0058-PCT_Seq_IDs.txt," created 11 Sep. 2008 comprising 4 KB is hereby incorporated herein.

BACKGROUND OF THE INVENTION

Approximately 50 million Americans suffer from chronic sleep disorders and an additional 20 to 30 million suffer from intermittent sleep disorders. Insomnia is the most common sleep disorder affecting approximately 10 to 17 percent of the American population. Insomnia is both a symptom (secondary to a medical, psychiatric, circadian, or sleep disorder) and a syndrome (primary insomnia that can not be attributable to other conditions). It is estimated that 25% of chronic insomnia is due to primary insomnia.

Insomnia is characterized by difficulty falling asleep or staying asleep resulting in nonrestorative sleep and daytime impairment. Difficulty sleeping is one of the symptoms of insomnia while daytime symptoms include sleepiness, impaired concentration, impaired memory, irritability and anxiety.

Based on the duration of symptoms, insomnia may be categorized as transient or long-term/chronic. Transient insomnia refers to sleep disturbances lasting from one night to a week. Transient insomnia can result from many emotional and environmental factors, including stress, environmental noise, medication side effects and sleep/wake schedule changes due to jet lag. In chronic insomnia, symptoms are present at least three times a week for up to one month or more. If left untreated, transient insomnia has the potential to progress to chronic insomnia.

While benzodiazepines have been used successfully to treat many forms of insomnia, side effects such as residual daytime sedation, rebound insomnia, amnesia, irritability and dependence are common. Non-benzodiazepine agents are becoming a more frequent and popular choice in the treatment of insomnia. These drugs act selectively on the benzodiazepine omega-receptor (zoldipem, Ambien®; zaleplon, Sonata®; zopiclone, Imovane®), or interacts with gamma-aminobutyric acid-(GABA) receptor complexes at binding domains located close to or allosterically coupled to benzodiazepine receptors (Eszopiclone, Lunesta®). Another drug used to treat insomnia, ramelteon, (Rozerem®) targets both melatonin receptors, MT1R and MT2R.

Melatonin, a hormone produced by the pineal gland during the hours of darkness, plays a major role in the synchronization of the sleep/wake cycle. The production of melatonin is regulated by a structure located in the hypothalamus called the suprachiasmatic nucleus (SCN). Melatonin affects a variety of target tissues and cells throughout the body by binding 2 high affinity receptors, MT1R and MT2R. One of the main sites of high-density melatonin receptor expression is the SCN itself. Thus, through complex internal pathways and continual exposure to external cues, human beings maintain a strong drive for daytime wakefulness and nighttime sleepiness. In addition to a chronobiotic effect, melatonin has a sleep promoting effect.

SUMMARY OF THE INVENTION

One aspect of the invention provides a method of predicting a sleep parameter of an individual, the method comprising: determining the individual's genotype at the PER3 variable number tandem repeat (VNTR) locus; and in the case that the individual's PER3 VNTR genotype is 5/5, predicting that the sleep parameter of the individual is indicative of better sleep than an individual whose PER3 VNTR genotype is 4/4 or 4/5.

Another aspect of the invention provides a method of treating a patient suffering from a sleep disorder or from insomnia as a symptom of another disorder, the method comprising: determining the patient's genotype at the PER3 variable number tandem repeat (VNTR) locus; and treating the patient based on the patient's PER3 VNTR genotype.

Another aspect of the invention provides a method of selecting individuals for inclusion in a sleep study, the method comprising: determining an individual's genotype for the PER3 VNTR locus; and in the case that the individual's PER3 VNTR genotype is 5/5, concluding that the individual will be less responsive to sleep-enhancing or sleep-inducing compositions than an individual having a PER3 VNTR genotype other than 5/5.

Yet another aspect of the invention provides (1R-trans)-N-[[2-(2,3-dihydro-4-benzofuranyl)cyclopropyl]methyl]propanamide for use in the treatment of a sleep disorder or one or more symptoms of insomnia associated with another disorder in a patient having a genotype associated with efficacious response to a sleep-inducing compound.

BRIEF DESCRIPTION OF THE DRAWINGS

FIGS. 1a-d show the responses of individuals with PER3 VNTR genotypes of 5/5 and non-5/5 (i.e., 4/4 or 4/5) following administration of (1R-trans)-N-[[2-(2,3-dihydro-4-benzofuranyl)cyclopropyl]methyl]propanamide during the course of a full night and the first, second, and third thirds of a night, respectively.

Figure 2:
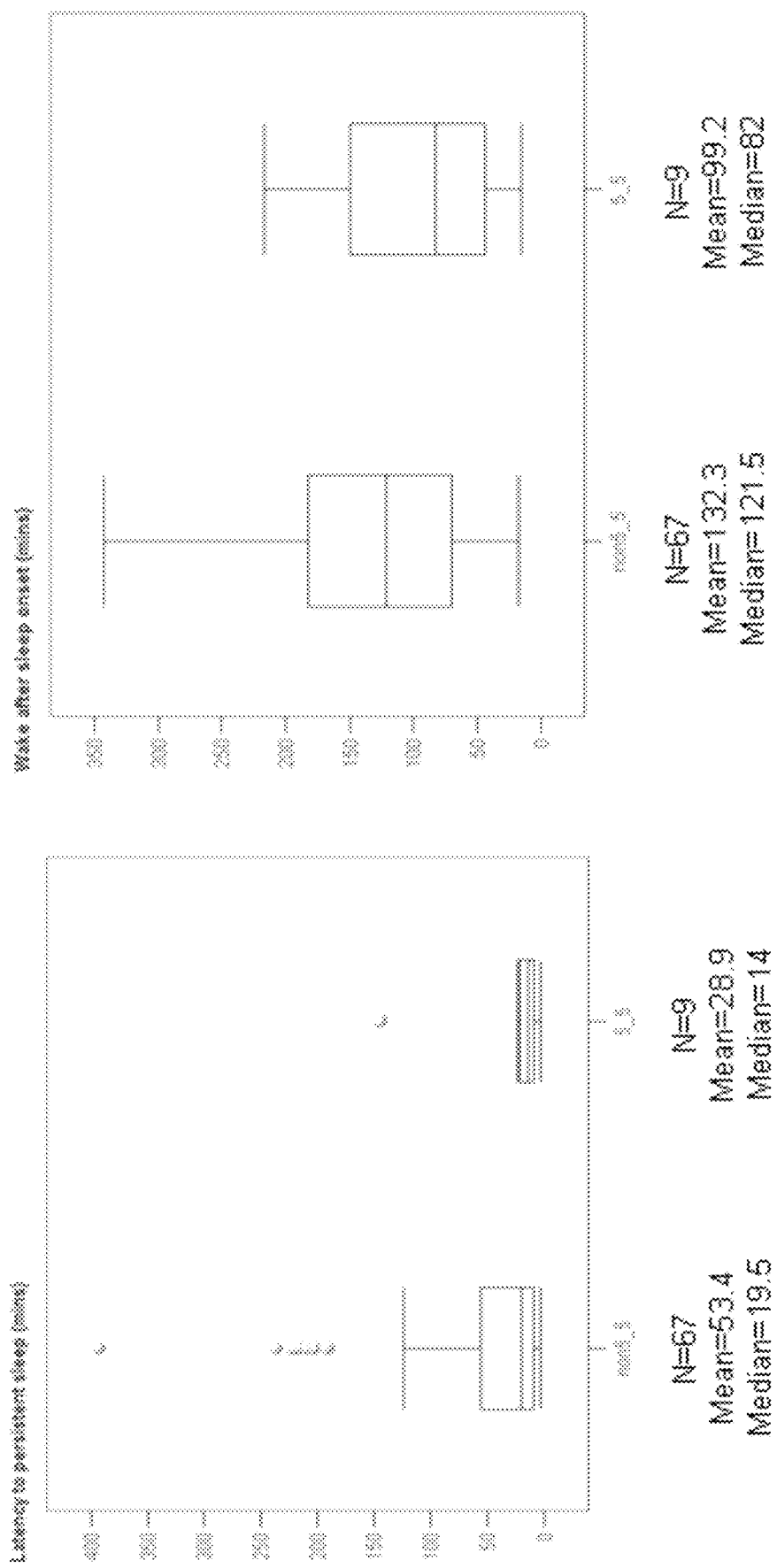
FIG. 2 shows the latency to persistent sleep (LPS) and wake after sleep onset (WASO) responses of PER3 VNTR 5/5 and non-5/5 individuals, in minutes.

DETAILED DESCRIPTION OF THE INVENTION (1R-trans)-N-[[2-(2,3-dihydro-4-benzofuranyl)cyclopropyl]methyl]propanamide (VEC-162) is a specific and potent agonist of the MT1R and MT2R melatonin receptors, currently in clinical development for the treatment of primary insomnia and circadian rhythm sleep disorders (CRSD). (1R-trans)-N-[[2-(2,3-dihydro-4-benzofuranyl)cyclopropyl]methyl]propanamide is disclosed in U.S. Pat. No. 5,856,529, which is incorporated by reference herein as though fully set forth. The structure of (1R-trans)-N-[[2-(2,3-dihydro-4-benzofuranyl)cyclopropyl]methyl]propanamide is shown below.

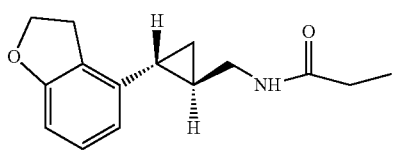 [SMILES: CCC(=O)NC[C@@H]1C[C@H]1c1cccc2c1CCO2]

(1R-trans)-N-[[2-(2,3-dihydro-4-benzofuranyl)cyclopropyl]methyl]propanamide is typically administered in immediate release form, but controlled release forms are included within the scope of the invention. The drug can be delivered alone or in combination with another active pharmaceutical ingredient.

The route of administration is usually oral although other routes of administration, e.g., parenteral, intravenous, intramuscular, buccal, lozenge, transdermal, transmucosal, etc., can be used. Controlled release forms, e.g., sustained, pulsatile, or delayed, including depot forms such as are disclosed in WO2003037337 or WO2004006886, can also be used.

Other melatonin agonists may also be used in practicing the present invention, including, for example, N-[1-(2,3-dihydrobenzofuran-4-yl)pyrrolidin-3-yl]-N-ethylurea], ramelteon ((S)—N-[2-(1,6,7,8-tetrahydro-2H-indeno-[5,4-b]furan-8-yl)ethyl]propionamide), LY156735 ((R)—N-(2-(6-chloro-5-methoxy-1H-indol-3yl)propyl)acetamide), Agomelatine (N-[2-(7-methoxy-1-naphthyl)ethyl]acetamide), 2-Phenylmelatonin, 8-M-PDOT, 2-Iodomelatonin, 6-Chloromelatonin, TAK-375, CGP 52608, GR196429, S20242, S-23478, S24268, S25150, GW-290569, Luzindole, GR135531, Melatonin Research Compound A, Melatonin Agonist A, Melatonin Analogue B, Melatonin Agonist C, Melatonin Agonist E, Melatonin Agonist G, Melatonin Agonist H, Melatonin Agonist I, Melatonin Analog J, Melatonin Analog K, Melatonin Analog L, AH-001, GG-012, Enol-3-IPA, ML-23, SL-18.1616, IP-100-9, Sleep Inducing Peptide A, AH-017, AH-002, BDD-40001, PD6735, Theanine, and IP-101. Many of these compounds are described in International Patent Application No. PCT/US07/69366, filed 21 May 2007, which is hereby incorporated by reference. The invention includes the use of metabolites or prodrugs of the above compounds, and any hydrates, conjugates, salts, esters, isomers, polymorphs, or analogues of the above compounds.

Metabolites of (1R-trans)-N-[[2-(2,3-dihydro-4-benzofuranyl)cyclopropyl]methyl]propanamide include, for example, those described in "Preclinical Pharmacokinetics and Metabolism of BMS-214778, a Novel Melatonin Receptor Agonist" by Vachharajani et al., J. Pharmaceutical Sci., 92(4):760-772, which is hereby incorporated herein. These metabolites include hydroxylated, dehydrogenated, glucuronide, and diol derivatives of (1R-trans)-N-[[2-(2,3-dihydro-4-benzofuranyl)cyclopropyl]methyl]propanamide.

The compositions are preferably formulated in an oral unit dosage form, each dosage containing from about 5 to about 100 mg of (1R-trans)-N-[[2-(2,3-dihydro-4-benzofuranyl)cyclopropyl]methyl]propanamide. The term "unit dosage form" refers to physically discrete units suitable as unitary dosages for human subjects, each unit containing a predetermined quantity of active material calculated to produce the desired prophylactic or therapeutic effect over the course of a treatment period, in association with the required pharmaceutical carrier. So, for example, an adult patient suffering a sleep disorder could be prescribed 1-4 tablets, each having about 5 mg to about 100 mg of (1R-trans)-N-[[2-(2,3-dihydro-4-benzofuranyl)cyclopropyl]methyl]propanamide for a total daily dose of about 10 mg/day to about 100 mg/day.

The term, "about" means, in general, a range of plus or minus ten percent, except that with respect to whole single digit or fractional values, the range is within plus or minus one of the last digit recited. Thus, "about 100" includes 90 to 110, "about 5" includes 4 to 6, and "about 1.5" includes 1.4 to 1.6. In no event can the term, "about," include a nonsensical value such as a value that exceeds 100% or is less than zero.

A number of genes have been implicated in the regulation of the circadian clocks, and their implication in sleep disorders and other medical conditions is increasingly recognized. The PER3 gene is a member of the Period family of genes which is expressed in a circadian pattern in the suprachiasmatic nucleus. Several polymorphisms have been described in the PER3 genes, including a variable number tandem repeat (VNTR) with 2 alleles of 4 or 5 repeats. This VNTR has been associated with diurnal preference and delayed-sleep phase syndrome (DSPS). Recently, it has also been demonstrated that this polymorphism predicts sleep structure and waking performance.

The effect of this polymorphism was investigated with respect to various sleep parameters (latency to persistent sleep, wake after sleep onset, sleep efficiency), which evaluated objectively by polysomnography in healthy subjects treated with (1R-trans)-N-[[2-(2,3-dihydro-4-benzofuranyl)cyclopropyl]methyl]propanamide, or treated with a placebo, in a clinical protocol that models transient insomnia. As will be explained in greater detail below, it was found that the PER3 VNTR polymorphisms had a significant effect on how individuals were affected by the induced transient insomnia protocol and their response to the (1R-trans)-N-[[2-(2,3-dihydro-4-benzofuranyl)cyclopropyl]methyl]propanamide treatment.

Transient insomnia can be induced in a laboratory setting as a result of a "first night effect" in which sleep onset and sleep maintenance are disrupted in normal sleeping adults by sleeping in an unfamiliar surrounding. This model of transient insomnia has been validated in several studies of normal sleeping adults. Insomnia can also be precipitated by other factors such as traveling across multiple time zones (jet lag). This condition can be reproduced in a sleep laboratory by forcing an earlier bedtime (phase advance). The study reported here used both, the first night effect and a 5-hour phase advance component, to increase the likelihood that transient insomnia will be induced. A multi-center, randomized, double-blind, placebo-controlled, parallel study was conducted to investigate the efficacy and safety of a single oral dose of (1R-trans)-N-[[2-(2,3-dihydro-4-benzofuranyl)cyclopropyl]methyl]propanamide (20 mg, 50 mg, and 100 mg) and matching placebo in healthy male and female subjects with induced transient insomnia. Previous studies showed that (1R-trans)-N-[[2-(2,3-dihydro-4-benzofuranyl)cyclopropyl]methyl]propanamide is well-tolerated by healthy volunteers in single doses up to 300 mg and in multiple doses (up to 28 days) up to 150 mg. Latency to Persistent Sleep (LPS), Wake After Sleep Onset (WASO) and sleep efficiency (SE) were evaluated objectively by use of polysomnography.

More than 70% of subjects who enrolled in the clinical trial consented to the optional PG study. From those, 288 were genotyped for the PER3 VNTR polymorphism.

The PER3 VNTR polymorphism after detected by a standard Polymerase Chain Reaction (PCR) using the following primers:
Forward (SEQ. ID No. 1): 5'-CAAAATTTTATGACACTACCAGAATGGCTGAC-3',
Reverse (SEQ. ID No. 1): 5'-AACCTTGTACTTCCACATCAGTGCCTGG-3'.
Following amplification, 5 μL of the PCR product was combined with 5 μL 2× gel loading dye, run on a 4% agarose gel, and genotypes were called based upon the appearance of either a 581 bp band (4/4 homozygote), a 635 bp band (5/5 homozygote), or both bands (4/5 heterozygote).

As reported in most other populations, the PER3$^4$ allele was the most common (~69%) in the overall study population. Frequencies of the PER3$^{4/4}$, PER3$^{4/5}$ and PER3$^{5/5}$ genotypes were 49%, 40%, and 11%, respectively. The PER3$^5$ allele was more frequent among the Black and African-American subjects (36%) than among Whites (29%), with a PER3$^{5/5}$ genotype frequency of 15% and 10%, respectively.

It was found that individuals with the PER3$^{5/5}$ genotype were less affected by the induced transient insomnia protocol than individuals with the PER3$^{4/4}$ or PER3$^{4/5}$ genotypes (FIG. 1a). More specifically, individuals with the PER3$^{5/5}$ genotype who received the placebo had an overall sleep efficiency of 77.6%, as compared to 66.4% for individuals with the PER3$^{4/4}$ or PER3$^{4/5}$ genotype. This difference was particularly significant in the first and second third of the night: 77.2% and 72.4%, respectively, for PER3$^{5/5}$ vs 58.8% and 60.5%, respectively, for other genotypes (FIGS. 1b-c). The genotype difference in overall sleep efficiency seen in the placebo-treated subjects reflected differences in both LPS and WASO. The mean LPS and WASO were 29 and 99 minutes, respectively, for placebo-treated subjects with the PER3$^{5/5}$ genotype vs 53 and 132 minutes, respectively, for individuals with a different genotype (FIG. 2).

Figure 3:
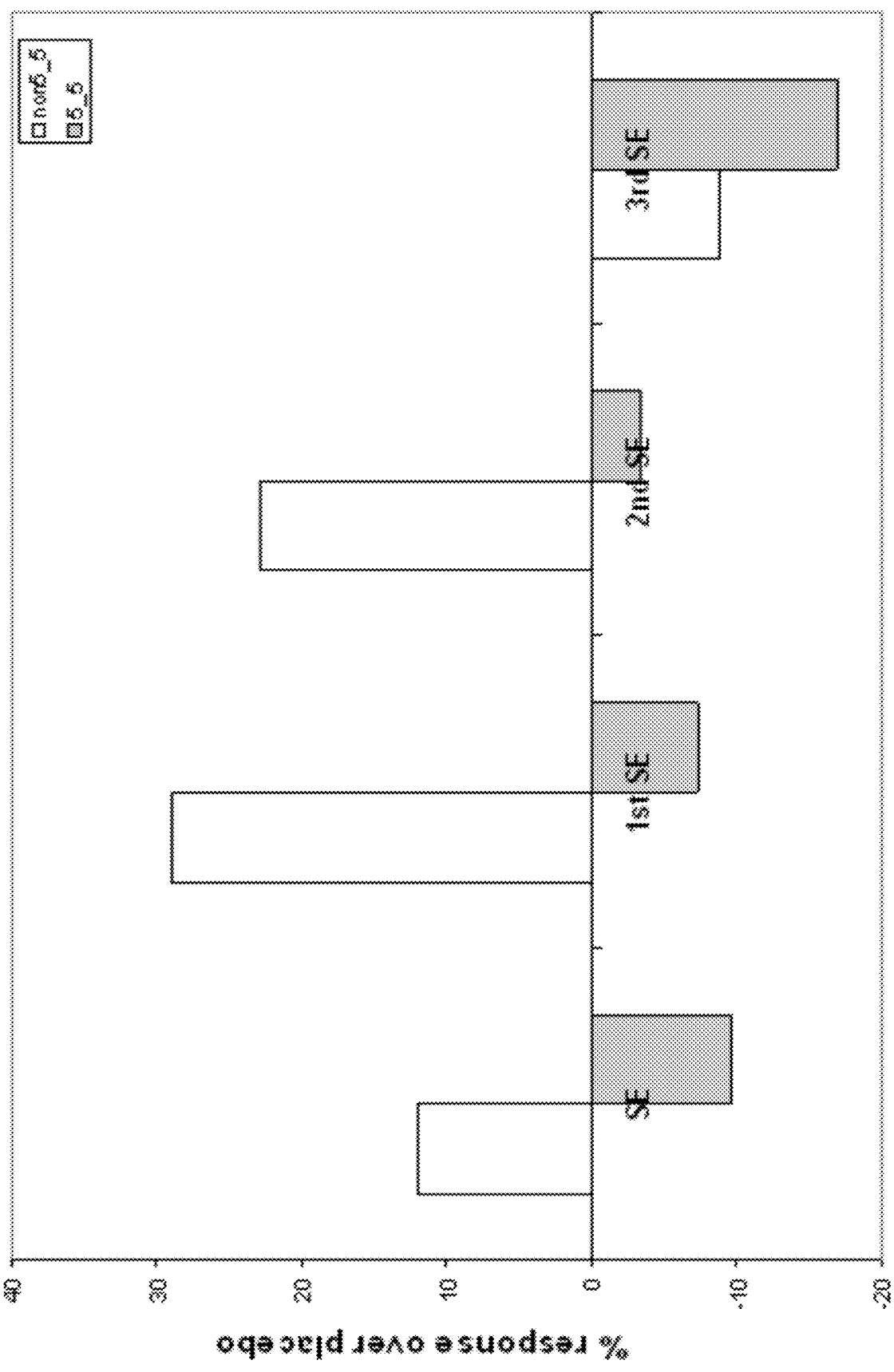
FIG. 3 shows the sleep efficiency (SE) responses of PER3 VNTR 5/5 and non-5/5 individuals.

(1R-trans)-N-[[2-(2,3-dihydro-4-benzofuranyl)cyclopropyl]methyl]propanamide was efficacious in improving LPS, WASO, and Sleep Efficiency. Individuals treated with (1R-trans)-N-[[2-(2,3-dihydro-4-benzofuranyl)cyclopropyl] methyl]propanamide with the PER3$^{4/4}$ and PER3$^{4/5}$, who were expected to be more affected by the transient insomnia protocol, had indeed a greater benefit from the treatment. They experienced 12% greater sleep efficiency over subjects on placebo, as compared with a 9.5% lower sleep efficiency for subjects with the PER3$^{5/5}$ genotype (FIG. 3). This genotype effect was particularly striking in the first and second third of the night with sleep efficiency 29% and 22.8% higher, respectively, than in placebo for the PER3$^{4/4}$ and PER3$^{4/5}$ genotypes, versus 7.2% and 3.4% lower, respectively, for the PER3$^{5/5}$ genotype (FIG. 3). There was no improvement in the third part of the night (FIG. 1d); however, the sleep efficiency of individuals treated with (1R-trans)-N-[[2-(2,3-dihydro-4-benzofuranyl)cyclopropyl] methyl]propanamide who carried the PERT" or PER3$^{4/5}$ genotype was still better than those with the PER3$^{5/5}$ genotype (FIG. 3).

Figure 4:
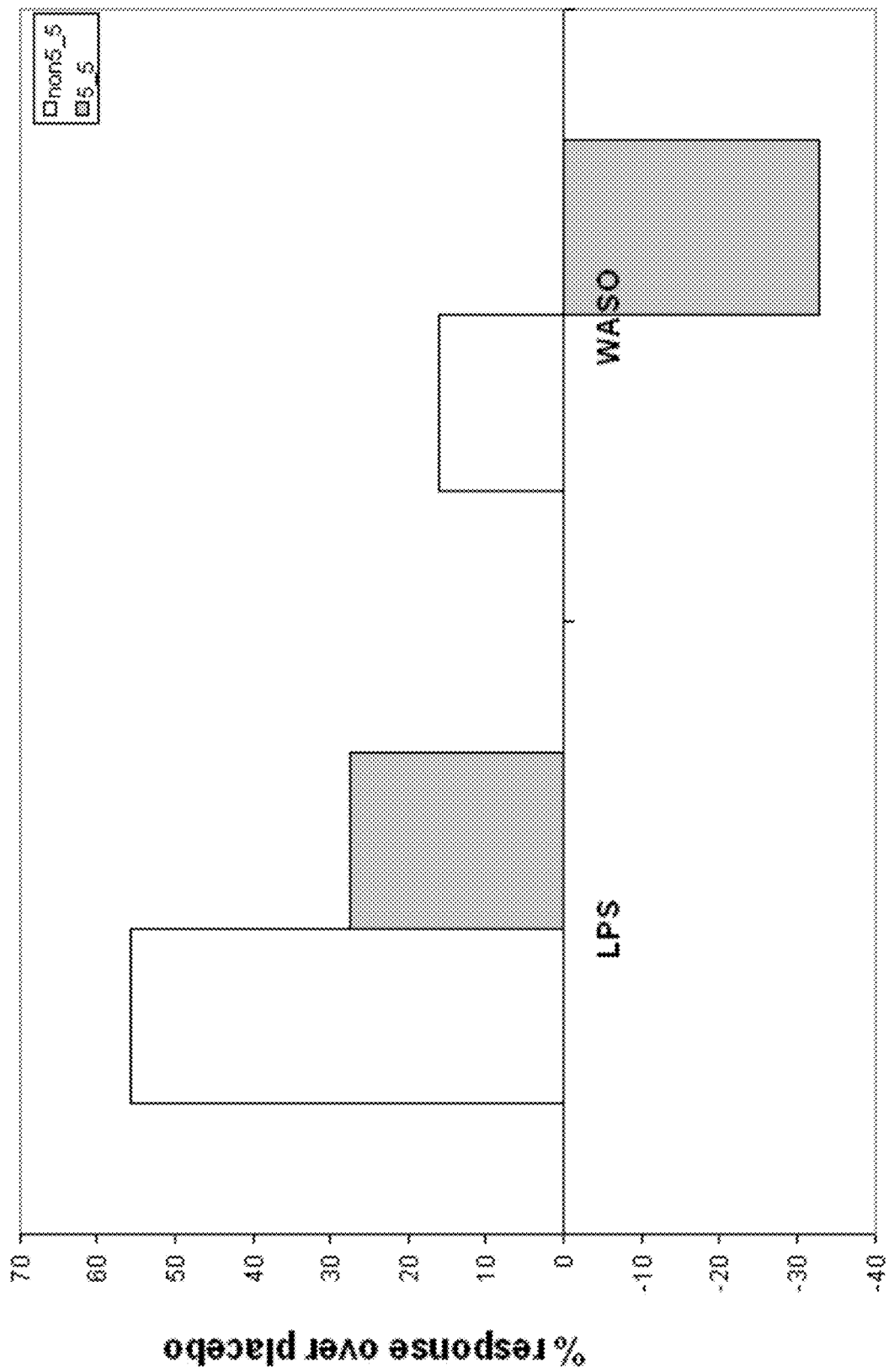
FIG. 4 shows the LPS and WASO responses of PER3 VNTR 5/5 and non-5/5 individuals, in percent response compared to placebo.

The effect of the PER3 genotype was also visible in the LPS and WASO measurements. PERT" and PER3$^{4/5}$ individuals had 30 minutes (56%) shorter LPS period and 21 minutes (16%) smaller WASO when treated with (1R-trans)-N-[[2-(2,3-dihydro-4-benzofuranyl)cyclopropyl]methyl] propanamide than with the placebo, as compared to only 8 minutes (27%) shorter LPS and a 32 minutes (32.7%) longer WASO for individuals with the PER3$^{5/5}$ genotype (FIG. 4).

An individual's genotype at the PER3 VNTR may be determined by any number of methods. For example, the genotype may be determined by analyzing the DNA sequence directly, as described above. Alternatively, the genotype may be determined by analyzing an RNA transcript (e.g., mRNA) or a gene expression product (e.g., a protein), as will be recognized by one skilled in the art. Genotyping is preferably performed ex vivo.

An effective amount, quantitatively, may vary, e.g., depending upon the patient, the severity of the disorder or symptom being treated, and the route of administration. Such dose can be determined by routine studies. In general, for systemic administration, e.g., oral administration, the dose of (1R-trans)-N-[[2-(2,3-dihydro-4-benzofuranyl)cyclopropyl]methyl]propanamide will be in the range of about 10 mg/day to about 100 mg/day, in one or more unit dosage forms.

It will be understood that the dosing protocol including the amount of (1R-trans)-N-[[2-(2,3-dihydro-4-benzofuranyl)cyclopropyl]methyl]propanamide actually administered will be determined by a physician in the light of the relevant circumstances including, for example, the condition to be treated, the chosen route of administration, the age, weight, and response of the individual patient, and the severity of the patient's symptoms. Patients should of course be monitored for possible adverse events.

Particle size will also affect the dose selected. At larger particle sizes, i.e., D50 is greater than about 100 µm, e.g., about 100 µm to about 200 µm, oral doses at the higher end, i.e., up to about 100 mg are effective, whereas at smaller particle sizes, i.e., D50 is less than about 100 µm, e.g., about 20 µm to about 50 µm, lower doses, i.e., less than about 100 mg, are useful, e.g., about 10 mg to about 80 mg and about 20 mg to about 50 mg. (Particle size measurements supporting the above were made laser diffraction using a Malvern Mastersizer. The D50 (D10, D90, D100) value means that 50% (10%, 90%, 100%) of the particles by weight are of the indicated diameter or smaller.) In one embodiment of the invention, the above doses are administered in immediate release form, i.e., a non-controlled release formulation.

If desired, doses can optionally be adjusted for body size using the following as guidance: useful amounts for larger particles are up to about 1.5 mg/kg; useful amounts for smaller particles include doses of less than about 1.5 mg/kg, e.g., about 0.1 mg/kg to about 1.2 mg/kg and about 0.3 mg/kg to about 0.7 mg/kg.

Treatment is continued until the patient's circadian rhythm is restored to normal, i.e., until the patient's normal daily functioning is not inhibited by the sleep disorder or until the patient is sleeping normally. Treatment can continue for some time after these end points are achieved so as to lessen the likelihood of relapse. For therapeutic or prophylactic use, (1R-trans)-N-[[2-(2,3-dihydro-4-benzofuranyl) cyclopropyl]methyl]propanamide will normally be administered as a pharmaceutical composition, (1R-trans)-N-[[2-(2,3-dihydro-4-benzofuranyl)cyclopropyl]methyl] propanamide comprising the (or an) essential active ingredient in association with a solid or liquid pharmaceutically acceptable carrier and, optionally, with pharmaceutically-acceptable adjuvants and excipients employing standard and conventional techniques. Pharmaceutically-acceptable salts of (1R-trans)-N-[[2-(2,3-dihydro-4-benzofuranyl)cyclopropyl]methyl]propanamide may similarly be used.

(1R-trans)-N-[[2-(2,3-dihydro-4-benzofuranyl)cyclopropyl]methyl]propanamide is very soluble or freely soluble in 95% ethanol, methanol, acetonitrile, ethyl acetate, isopropanol, polyethylene glycols (PEG-300 and PEG-400), and only slightly soluble in water. The native pH of a saturated solution of (1R-trans)-N-[[2-(2,3-dihydro-4-benzofuranyl) cyclopropyl]methyl]propanamide in water is 8.5 and its aqueous solubility is practically unaffected by pH.

Pharmaceutical compositions useful in the practice of this invention include suitable dosage forms for oral, parenteral (including subcutaneous, intramuscular, intradermal and intravenous), transdermal, bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of (1R-trans)-N-[[2-(2,3-dihydro-4-benzofuranyl)cyclopropyl]methyl]propanamide in oral dosage formulations. The pharmaceutical compositions may be prepared by conventional techniques appropriate to the desired preparation containing appropriate amounts of (1R-trans)-N-[[2-(2,3-dihydro-4-benzofuranyl) cyclopropyl] methyl]propanamide. See, for example, Remington's Pharmaceutical Sciences, Mack Publishing Company, Easton, Pa., 17th edition, 1985.

In making pharmaceutical compositions for use in the invention, the active ingredient(s) will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient, or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

A typical unit dose form could be size 0 or size 1 capsule comprising 20, 50, or 100 mg of (1R-trans)-N-[[2-(2,3-dihydro-4-benzofuranyl)cyclopropyl]methyl]propanamide in addition to anhydrous lactose, microcrystalline cellulose, silicon dioxide colloidal, croscarmellose sodium, and magnesium stearate. Storage at 15 to 20° C. with protection from moisture and sunlight is recommended.

In accordance with one embodiment of this invention, the D50 of the (1R-trans)-N-[[2-(2,3-dihydro-4-benzofuranyl) cyclopropyl]methyl]propanamide administered is less than about 100 µm, for example, about 20 µm to about 50 µm or about 30 µm to 40 µm.

(1R-trans)-N-[[2-(2,3-dihydro-4-benzofuranyl)cyclopropyl]methyl]propanamide can also be formulated in a controlled release form, e.g., delayed, sustained, or pulsatile release. (1R-trans)-N-[[2-(2,3-dihydro-4-benzofuranyl)cyclopropyl]methyl]propanamide can also be administered concomitantly with other drug therapies, including but not limited to antidepressant drug therapies or other drug therapies for treating other emotional disorders. So, for example, the invention encompasses administration of (1R-trans)-N-[[2-(2,3-dihydro-4-benzofuranyl)cyclopropyl]methyl]propanamide in combination with other melatonergic agonists or other sleep-inducing agents.

An additional aspect of the invention is a kit for determining treatment strategy for a patient with a sleep disorder or from insomnia as a symptom of another disorder. Such kit is useful, e.g., in predicting a patient's response to treatment with (1R-trans)-N-[[2-(2,3-dihydro-4-benzofuranyl)cyclopropyl]methyl]propanamide, and, on the basis of such prognosis, treating the patient with a lower or higher dose of (1R-trans)-N-[[2-(2,3-dihydro-4-benzofuranyl)cyclopropyl] methyl]propanamide, treating the patient with (1R-trans)-N-[[2-(2,3-dihydro-4-benzofuranyl)cyclopropyl]methyl]propanamide in combination with other therapies, or choosing a different treatment altogether.

A kit of the invention is a combination of physical elements, e.g., probes, including without limitation specific primers, labeled nucleic acid probes, antibodies, protein-capture agent(s), reagent(s), instruction sheet(s) and other elements useful to practice the invention, in particular, to identify the alleles present in the genetic locus described herein.

A kit of the invention may include at least one reagent specific for detecting a patient's genotype at the PER3 VNTR locus, as described elsewhere herein. Detection can be direct, e.g., by directly sequencing the relevant portion of a person's chromosomal DNA, or indirect, e.g., by sequencing messenger RNA transcripts or by sequencing gene expression products, i.e., polypeptides. Thus, the reagent may be, e.g., a polynucleotide, or an array of polynucleotides, or an antibody or a panel of antibodies.

The kit may also comprise one or more gene specific genotyping primer composition. The primer composition can comprise at least one gene specific genotyping polynucleotide. The composition can comprise two or more sets of allele specific primer pairs. The two allele specific genotyping oligonucleotides may be packaged in separate containers. In some embodiments, degenerate primer sets are provided for amplification.

In another embodiment, the kit may optionally include instructions for isoelectric focusing methods for detecting and distinguishing gene expression products.

Antibody based kits can comprise, e.g., an antibody that is specific for the gene expression product of a given allele and that is bound to a solid support; and a second antibody that binds the gene expression product and that is conjugated to a detectable group.

The kit may also comprise reagents such as buffering agents, hybridization buffers, and protein or nucleic acid stabilizing agents, e.g., polysaccharides and the like. If carrying out the assay requires amplification of DNA or RNA, such as by PCR, then the kit may also comprise a polymerase or a reaction buffer. The kit may be packaged in any suitable manner, typically with all elements in a single container along with a sheet of printed instructions for carrying out the test or for interpreting results.

The foregoing description of various aspects of the invention has been presented for purposes of illustration and description. It is not intended to be exhaustive or to limit the invention to the precise form disclosed, and modifications and variations are possible. Such modifications and variations are intended to be included within the scope of the invention as defined by the accompanying claims.

What is claimed is:

1. A method of treating a patient suffering from a sleep disorder or from insomnia as a symptom of another disorder, the method comprising:
    determining the patient's genotype at the PER3 variable number tandem repeat (VNTR) locus to be 4/5; and
    treating the patient by administering to the patient an effective amount of (1R-trans)-N-[[2-(2,3-dihydro-4-benzofuranyl)cyclopropyl]methyl]propanamide.

2. The method of claim 1, wherein the effective amount is sufficient to improve at least one sleep parameter of the patient selected from a group consisting of: sleep efficiency (SE), total sleep time (TST), latency to persistent sleep (LPS), and wake after sleep onset (WASO).

3. The method of claim 1, wherein the effective amount is between about 10 mg/day and about 300 mg/day.

4. The method of claim 3, wherein the effective amount is between about 10 mg/day and about 100 mg/day.

5. The method of claim 4, wherein the effective amount is between about 20 mg/day and about 50 mg/day.

6. The method of claim 5, wherein the effective amount is about 20 mg/day.

7. The method of claim 1, wherein the insomnia is selected from a group consisting of: chronic insomnia and transient insomnia.

* * * * *